US00PP30017P2

(12) United States Plant Patent
Head et al.

(10) Patent No.: US PP30,017 P2
(45) Date of Patent: Dec. 25, 2018

(54) JUNIPER PLANT NAMED 'RLH-SS1PI'

(50) Latin Name: *Juniperus silicicola*
Varietal Denomination: RLH-SS1PI

(71) Applicants: Robert Harold Head, Seneca, SC (US); Lisa Jones Head, Seneca, SC (US)

(72) Inventors: Robert Harold Head, Seneca, SC (US); Lisa Jones Head, Seneca, SC (US)

(73) Assignee: HEAD'S SELECT INC., Seneca, SC (US)

( * ) Notice: Subject to any disclaimer, the term of this patent is extended or adjusted under 35 U.S.C. 154(b) by 0 days.

(21) Appl. No.: 15/731,817

(22) Filed: Aug. 7, 2017

(51) Int. Cl.
*A01H 7/00* (2006.01)

(52) U.S. Cl.
USPC ..... Plt./214

(58) Field of Classification Search
USPC ..... Plt./214
See application file for complete search history.

*Primary Examiner* — Keith O. Robinson
(74) *Attorney, Agent, or Firm* — C. A. Whealy

(57) ABSTRACT

A new and distinct cultivar of Juniper plant named 'RLH-SS1PI', characterized by its relatively compact and upright narrowly pyramidal plant form; freely branching habit requiring minimal pruning; dense and bushy appearance; lateral branches that are flexible and resist breakage and splitting; leaves that maintain their bluish green color throughout the seasons; and good landscape performance.

1 Drawing Sheet

Botanical designation: *Juniperus silicicola.*
Cultivar denomination: 'RLH-SS1PI'.

BACKGROUND OF THE INVENTION

The present Invention relates to a new and distinct cultivar of Juniper plant, botanically known as *Juniperus silicicola*, and hereinafter referred to by the name 'RLH-SS1PI'.

The new Juniper plant is a product of a planned breeding program conducted by the Inventors in Long Creek, Oconee County, S.C. The new Juniper plant originated from an open-pollination in Long Creek, Oconee County, S.C., of a proprietary cultivar of *Juniperus silicicola* identified as MBSC-1, not patented, as the female, or seed, parent with an unknown selection of *Juniperus silicicola* as the male, or pollen, parent. The new Juniper plant was discovered and selected by the Inventors as a single plant from within the progeny of the stated open-pollination in a controlled environment in Long Creek, Oconee County, S.C. in 1995.

Asexual reproduction of the new Juniper plant by semi-hardwood and hardwood stem cuttings taken in a controlled environment in Long Creek, Oconee County, S.C. since 2000 has shown that the unique features of this new Juniper plant are stable and reproduced true to type in successive generations.

SUMMARY OF THE INVENTION

Plants of the new Juniper have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'RLH-SS1PI'. These characteristics in combination distinguish 'RLH-SS1PI' as a new and distinct cultivar of Juniper plant:

1. Relatively compact and upright narrowly pyramidal plant form.
2. Freely branching habit requiring minimal pruning; dense and bushy appearance.
3. Lateral branches that are flexible and resist breakage and splitting.
4. Leaves that maintain their bluish green color throughout the seasons.
5. Good landscape performance.

Plants of the new Juniper can be compared to plants of the female parent, 'MBSC-1'. Plants of the new Juniper differ primarily from plants of 'MBSC-1' in the following characteristics:

1. Plants of the new Juniper are more compact than plants of 'MBSC-1'.
2. Plants of the new Juniper have an upright narrowly pyramidal plant form whereas plants of 'MBSC-1' have a broad dome-shaped plant form.

Plants of the new Juniper can also be compared to plants of *Juniperus virginiana* 'Burkii', not patented. Plants of the new Juniper differ primarily from plants of 'Burkii' in the following characteristics:

1. Plants of the new Juniper are more compact and have a slower growth rate than plants of 'Burkii'.
2. Plants of the new Juniper have a narrowly pyramidal and dense plant form whereas plants of 'Burkii' have a broadly pyramidal and open plant form.
3. Lateral branches of plants of the new Juniper are flexible whereas lateral branches of plants of 'Burkii' are stiff and rigid and prone to breakage and splitting.
4. Plants of the new Juniper have shorter leaves than plants of 'Burkii'.
5. Leaves of plants of the new Juniper maintain their bluish green color throughout the year whereas leaves of plants of 'Burkii' are greyish green in color during the summer and become purple to bronze-green in color with freezing temperatures.

6. Leaves of plants of the new Juniper are soft and flexible whereas leaves of plants of 'Burkii' are stiff, rigid and sharp to the touch.
7. Plants of the new Juniper produce fewer and smaller cones than plants of 'Burkii'.

BRIEF DESCRIPTION OF THE PHOTOGRAPH

The accompanying colored photograph illustrates the overall appearance of the new Juniper plant showing the colors as true as it is reasonably possible to obtain in colored reproductions of this type. Colors in the photograph may differ slightly from the color values cited in the detailed botanical description which accurately describe the colors of the new Juniper plant.

The photograph is a side perspective view of a typical plant of 'RLH-SS1PI' grown in an outdoor nursery.

DETAILED BOTANICAL DESCRIPTION

Plants used for the aforementioned photograph and following observations and measurements were grown during the summer in ground beds in an outdoor nursery in Seneca, S.C. Plants were grown under partial to full sunlight conditions and cultural practices typical of commercial Juniper plant production. During the production of the plants, day temperatures ranged from −5° C. to 45° C. and night temperatures ranged from −25° C. to 35° C. Plants were 16 years old when the photographs and description were taken. In the following description, color references are made to The Royal Horticultural Society Colour Chart, 2007 Edition, except where general terms of ordinary dictionary significance are used.

Botanical classification: *Juniperus silicicola* 'RLH-SS1PI'.

Parentage:

*Female, or seed, parent.*—*Juniperus silicicola* 'MBSC-1', not patented.

*Male, or pollen, parent.*—Unknown selection of *Juniperus silicicola*, not patented.

Propagation:

*Type.*—By semi-hardwood and hardwood cuttings.

*Time to initiate roots.*—About 45 to 90 days at temperatures about 8° C. to 17° C.

*Time to produce a rooted cutting.*—About 120 to 180 days at temperatures about 8° C. to 17° C.

*Root description.*—Thick to thin; coarse, fibrous and cord-like; initially white, close to 155C becoming closer to 165C to 165D with development; actual color of the roots is dependent on substrate composition, water quality, fertilizer type and formulation, substrate temperature and physiological age of roots.

*Rooting habit.*—Freely branching; medium density.

Plant description:

*Plant form and growth habit.*—Perennial evergreen conifer tree; relatively compact and upright narrowly pyramidal plant form; moderate growth rate and good plant vigor.

*Branching habit.*—Freely branching habit requiring minimal pruning; dense and bushy appearance; lateral branches are flexible and resist breakage and splitting.

*Plant height.*—About 6.8 meters.

*Plant diameter.*—About 2.5 meters.

*Lateral branch description.*—Length: About 1.5 cm to 10.5 cm. Diameter: About 0.8 mm to 2.3 cm. Internode length: About 2 mm to 8 mm. Strength: Strong, flexible. Aspect: Upright to outwardly. Texture: Four-sided, glabrous. Strength: Strong. Color, developing: Close to 136C. Color, mature: Close to 165A.

*Leaf description.*—Arrangement: Opposite to whorled; simple; sessile. Length: About 1 mm to 2.2 mm. Width: About 0.5 mm to 1.5 mm. Shape: Scale-like. Apex: Minutely aristulate, blunt. Base: Broad, flat. Margin: Entire. Texture, upper and lower surface: Smooth, glabrous; soft to the touch. Venation pattern: Parallel. Color: Developing leaves, upper surface: Close to 133C to 133D. Developing leaves, lower surface: Close to 133D. Fully expanded leaves, upper surface: Close to 133C to 133D; venation, close to 133C to 133D; leaf color is maintained throughout the seasons. Fully expanded leaves, lower surface: Close to 133C; venation, close to 133C; leaf color is maintained throughout the seasons.

*Cone description.*—Quantity: About 25% of the branchlets produce a single small male cone. Time of development: Cones develop during the late autumn to winter and release pollen from mid-winter to late winter. Length: About 1 mm to 4 mm. Diameter: About 0.8 mm to 1.8 mm. Color: Close to N167B. Stamen quantity: About three to six. Filament length: About 0.1 mm to 0.2 mm. Filament color: Close to N167B. Anther length: About 0.1 mm to 0.2 mm. Anther shape: Oval to rounded. Anther color: Close to N167B. Pollen amount: Moderate. Pollen color: Close to 19C.

Pathogen & pest resistance: Plants of the new Juniper have been observed to have tolerance to Juniper Twig Blight (*Phomopsis juniperovora*). Plants of the new Juniper have not been noted to be resistant to pests or other pathogens common to Juniper plants.

Landscape performance: Plants of the new Juniper have been observed to have good landscape performance and to be tolerant to dry conditions, high humidity and temperatures ranging from about −30° C. to about 45° C.

It is claimed:

1. A new and distinct Juniper plant named 'RLH-SS1PI' as illustrated and described.

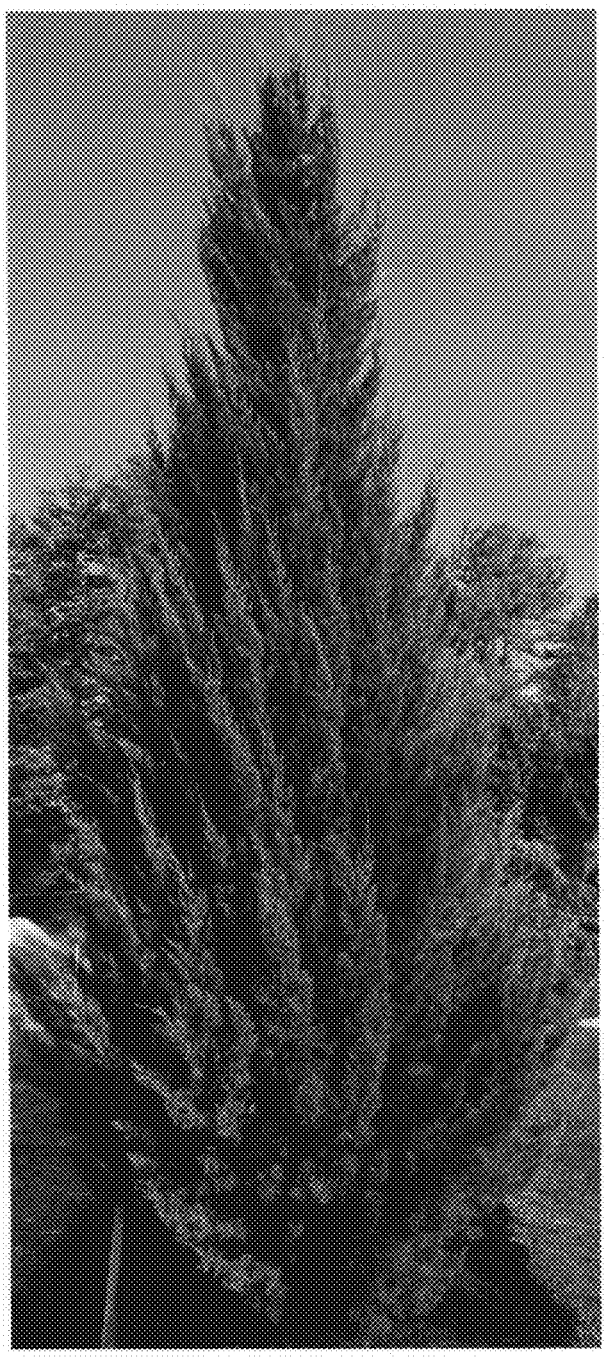

* * * * *